United States Patent [19]

Naples et al.

[11] Patent Number: 4,602,624
[45] Date of Patent: Jul. 29, 1986

[54] IMPLANTABLE CUFF, METHOD OF MANUFACTURE, AND METHOD OF INSTALLATION

[75] Inventors: Gregory G. Naples, Brecksville; James D. Sweeney; J. Thomas Mortimer, both of Cleveland Heights, all of Ohio

[73] Assignee: Case Western Reserve University, Cleveland, Ohio

[21] Appl. No.: 659,824

[22] Filed: Oct. 11, 1984

[51] Int. Cl.[4] .......................... A61N 1/04; A61B 5/04
[52] U.S. Cl. .................................................. 128/784
[58] Field of Search ............... 128/419 C, 419 R, 642, 128/784–785, 802

[56] References Cited

U.S. PATENT DOCUMENTS

| | | | |
|---|---|---|---|
| Re. 26810 | 3/1970 | Schwartz et al. | 128/784 |
| 415,274 | 11/1889 | Kane | 128/389 |
| 3,157,181 | 11/1964 | McCarty | 128/784 |
| 3,654,933 | 4/1972 | Hagfers | 128/784 |
| 3,738,368 | 6/1973 | Avery et al. | 128/784 |
| 3,774,618 | 11/1973 | Avery | 128/784 |
| 4,094,309 | 6/1978 | Grzenia | 128/644 |
| 4,341,221 | 7/1982 | Testerman | 128/642 |

OTHER PUBLICATIONS

"A Technique For Collision Block of Peripheral Nerve: Single Stimulus Analysis", IEEE Trans on Biomed. Eng., vol. BME-28, No. 5, May 1981.
"A Technique For Collision Block of Peripheral Nerve: Frequency Dependence", IEEE Trans on Biomed. Engr. vol. BME-28, No. 5, May 1981.
"Generation of Unidirectionally Propagated Action Potentials in a Peripheral Nerve by Brief Stimuli", Science, vol. 206, pp. 1311-1312, Dec. 1979.

*Primary Examiner*—William E. Kamm
*Assistant Examiner*—Mitchell J. Shein
*Attorney, Agent, or Firm*—Fay, Sharpe, Fagan, Minnich & McKee

[57] ABSTRACT

A self-curling sheet (A) of non-conductive material is biased to curl into a tight spiral. A cut out (22) is removed from one corner of the sheet such that, when the sheet spirals, a passage (28) defined axially therethrough has one portion with a smaller diameter and another portion with a larger diameter. A pair of conductive strips (40, 50) are disposed on the self-curling sheet such that one extends peripherally around each of the larger and smaller diameter regions of the passage therethrough. The conductive segments may be electrically conductive for applying electrical impulses or fluid conductive for infusing medications. In use, a first edge (14) of the self-curling sheet is disposed adjacent a nerve trunk which is to receive the cuff therearound. The self-curling sheet is controllably permitted to curl around the nerve forming an annular cuff therearound.

19 Claims, 6 Drawing Figures

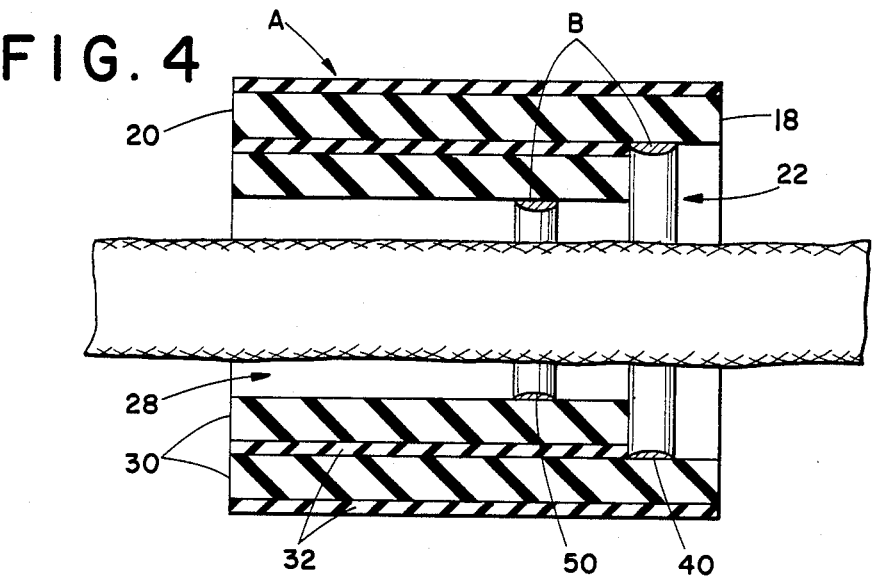
FIG. 4
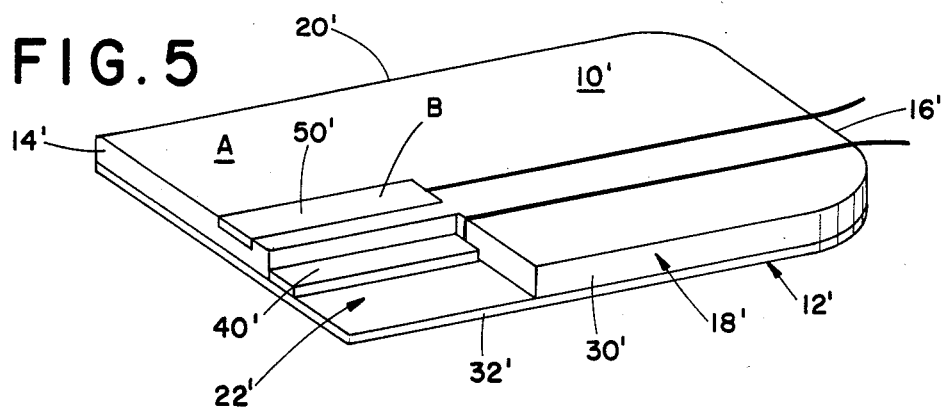
FIG. 5
FIG. 6

IMPLANTABLE CUFF, METHOD OF MANUFACTURE, AND METHOD OF INSTALLATION

BACKGROUND OF THE INVENTION

The present invention relates to the biomedical arts, particularly implantable cuffs. The present invention finds application in electrodes disposed around nerve trunks and other small tissue strands and will be described with reference thereto. It is to be appreciated that the invention is also applicable to medicinal infusers and other implanted biomedical devices for introducing, monitoring, or removing matter or energy.

Functional electrical stimulation of the nervous system has been shown in recent years to offer great hope in restoring some degree of lost sensory and motor function in stroke victims and individuals with spinal cord lesions. Ways in which functional electrical stimulation can be utilized to restore a particular function include: (1) the use of surface electrodes to activate the nerves in the general region of interest; (2) the use of intramuscular electrodes, also to activate the nerves in a general region; and (3) the use of nerve cuff electrodes placed around specific nerves of interest and used to activate them specifically. The third alternative offers advantages over the first two in that it requires the least amount of stimulating current and hence charge injected into the tissue. In addition, it allows easy excitation of entire muscles rather than parts of muscles, a common situation for the first two categories. Because the use of nerve cuff electrodes requires delicate surgery, they are usually contemplated only when: (1) excitation of specific, isolated muscles is desired; or (2) the generation of unidirectional action potentials is required.

The prior art cuff electrodes included a cylinder of dielectric material defining a bore therethrough of sufficient diameter to receive the nerve trunk to be electrically stimulated. The cylinder had a longitudinal split or opening for receiving a nerve. During installation, the longitudinal split was sutured or otherwise held closed. Although suturing held the cuff in place, an electric current path was defined through the split which permitted current leakage. Two or three annular electrodes were positioned on the inner surface of the bore for use in applying the electrical stimuli. The electric stimuli, for example, may provide functional electrical stimulation, may block natural nerve pulses traveling along the nerve trunk, or the like.

The present invention contemplates a new and improved cuff which is readily installed and removed without damaging the nerve trunk or other tissue.

SUMMARY OF THE INVENTION

In accordance with the present invention, a cuff is provided for encircling a nerve trunk or other body tissue with at least one medication or electrical energy conductive member and a non-conductive sleeve extending to either side of the conductive member. The cuff includes a self-curling sheet of non-conductive material which is self-biased to curl into a tight spiral or roll. At least one conductive member is disposed adjacent one edge of the self-curling sheet.

In accordance with another aspect of the invention, the self-curling cuff of the above-described construction is held flat with the conductive member edge adjacent the body tissue to receive the cuff. Thereafter, the self-curling sheet is permitted to curl into a tubular spiral around the body tissue.

A primary advantage of the present invention is that it can be easily installed and removed on a nerve or other body tissue.

Another advantage is that leakage currents are minimized.

A further advantage of the present invention is that it compensates for variations and expansion in the diameter of the surrounded tissue.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts or in various steps and arrangements of steps. The figures and the described structures and methods are only for purposes of illustrating a preferred embodiment of the invention and are not to be construed as limiting it.

FIG. 4 is a side sectional view of the cuff in the curled configuration of FIG. 3 disposed around a body tissue fiber;

FIG. 5 is an alternate embodiment of a cuff in accordance with the present invention; and, FIG. 6 is another alternate embodiment of an cuff in accordance with the present invention.

DETAILED DESCRIPTION OF THE PREFERRED EMBODIMENT

Figure 1:
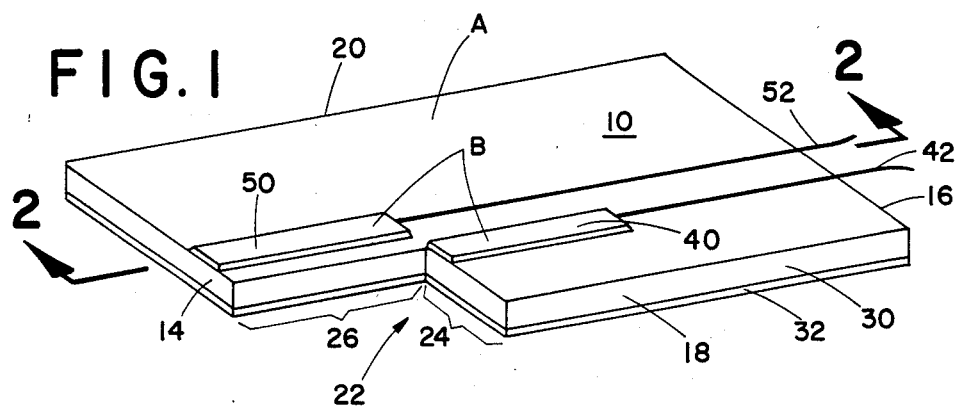
FIG. 1 is a perspective view of a self-curling cuff in accordance with the present invention constrained to a generally flat, uncurled configuration.
Figure 2:
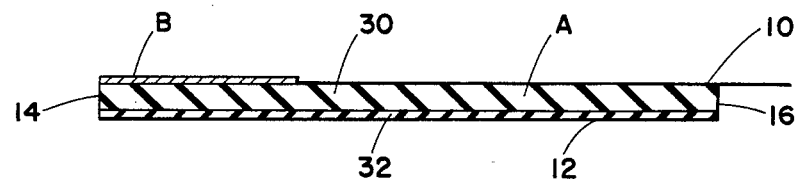
FIG. 2 is a sectional view through section 2—2 of FIG. 1.
Figure 3:
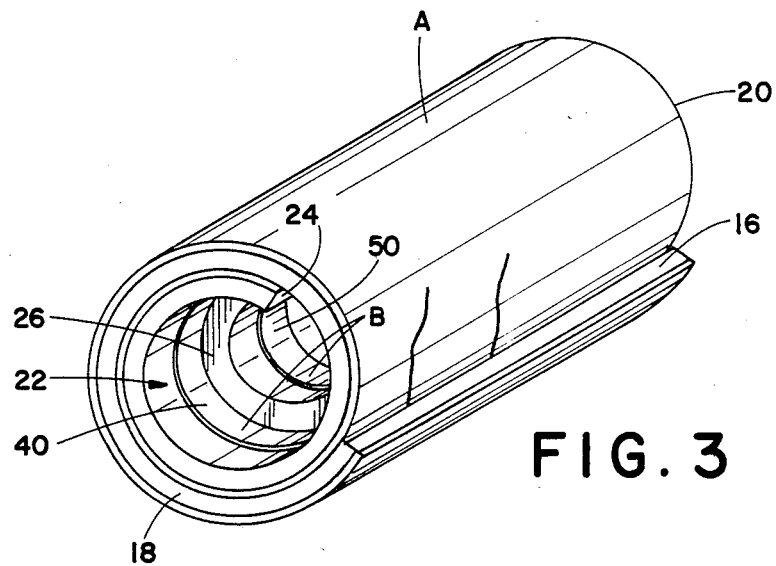
FIG. 3 is a perspective view of the cuff of FIG. 1 in a curled configuration.

With reference to FIGS. 1 and 2, an implantable cuff includes a self-curling non-conductive sheet A to which one or more conductive segments B are attached or embedded. The self-curling sheet is self-biased to curl into a tubular spiral or roll as illustrated in FIGS. 3 and 4.

Referring again to FIGS. 1 and 2, the self-curling sheet A includes a first generally planar surface 10 and an oppositely disposed second generally planar surface 12. In the preferred embodiment, the self-curling sheet is generally rectangular and extends from a first edge 14 to an oppositely disposed second edge 16 and from a first or arresting end 18 to an oppositely disposed second or escape end 20. A cut out region 22 is disposed adjacent the intersection of the first edge 14 and the first end 18. The cut out region has a longitudinal or first dimension or surface 24 parallel to the first edge which is equal to the width of an electrode plus the width of desired spacing between an electrode and the first end. The cut out further includes a transverse or second dimension or surface 26 parallel to the first end which is equal to the circumference of an inner axial passage 28 through the curled cuff or a multiple thereof. In this manner, edge 14 is disposed adjacent the edge of the cut out region when the sheet is curled. As illustrated in FIG. 4, the cut out region 22 translates into an enlarged diameter region 22 of the axial passage adjacent the first end 18 of the curled cuff.

In the preferred embodiment, the self-curling sheet is self-biased to curl by a first layer 30 and a second layer 32 of dissimilar size. As described in greater detail below, the first layer 30 is an elastomeric material which is stretched transversely between first and second edges 14 and 16 before it is laminated to the second layer 32. When the first layer is relaxed, it tries to contract but the second layer holds the adjoining surface stretched. More particularly, the first surface 10 contracts smaller than the second surface 12 causing the sheet A to curl. In the preferred embodiment, the first and second layers are both curled silicone rubbers adhered together by an adhesive layer, such as silicone rubber, epoxy, or the like. The layers may be assembled uncured and be air cured, temperature cured, vulcanized, or the like, after fabrication.

Other biocompatible materials are contemplated. For example, the stretchable first sheet 30 may be cured silicone rubber and the second sheet 32 may be a TEFLON film, a platinum mesh, or other bicompatible sheet. As yet another alternative, the stretched first layer may also be a non-rubber polymeric material which is both biocompatible and evidences appropriate elastomeric properties. It is to be appreciated, that in the figures the thickness of the sheets are exaggerated for simplicity of illustration.

The conductive segments B are disposed in, on, or below the first sheet 30. In the embodiment of FIGS. 1–4, in which the cuff is ideally configured for applying blocking electrical stimuli to nerves, the segments B are electrically conductive. The conductive segments include a first segment or segment 40 disposed adjacent the cut out region and extending transversely, i.e., parallel to the first end 18. The first electrode 40 has a width commensurate with the desired electrode and has a length commensurate with the circumference of the enlarged area 22 in the curled configuration of FIG. 3 such that the electrode extends peripherally around the body tissue. In preferred usage, the electrode 40 functions as an anode. A conductive lead 42 extends from the electrode portion to the second edge 16 for interconnection with an appropriate source of electrical potential. The lead may be welded to the electrode, integral with the electrode, or the like.

A second segment or electrode 50 is disposed adjacent the cut out area and extends generally the circumference of bore. When the cut out is a multiple of the bore circumference, the conductive member is a corresponding inverse integral fraction of the cut out end surface 26. This enables the second electrode to extend peripherally around an inner or smaller diameter portion of the axial passage 28 closely adjacent a nerve trunk. A conductive lead 52 such as a thin wire or strip of electrically conductive material extends to the second edge for connection with other lead wires and/or to an appropriate source of electrical potential. Most commonly, the second electrode is connected to function as a cathode. In the preferred embodiment, both electrodes are disposed closer to the first end 18 than the second end 20 such that a relatively long length of insulative sheath extends between the second electrode 50 and the escape end 20. This elongated insulative sheath inhibits electric current from flowing around the exterior of the sheath between the electrodes through electrically conductive body tissues and fluids rather than along the shortest path therebetween.

The electrically conductive regions are relatively thin. Ideally, the conductive regions are the thinnest layer which still conducts the amount of electrically required to be conducted by the electrodes. The conductive region may be a conductive polymer, a conductive paint, a very thin layer of metal, or thin wires. The thin metal layer may be vacuum deposited, sputtered, a thin or ultra-thin foil, or the like. The electrically conductive layers are also biocompatible such as platinum, gold, irridum, stainless steel, or the like.

Looking to specific details of an exemplary method of cuff manufacture, a sheet of cured silicone elastomer 30 which has a thickness of 0.005 inches is fixed at opposite ends by clamps. Sheets of other thickness can also be used. The sheet is then stretched across a steel plate, six inches long. The length of the exposed sheeting between the clamps in the unstretched state is varied according to the final diameter of the desired cuff. A shorter length of unstretched sheeting results in a greater amount of stretch and a smaller final cuff diameter.

After the first sheet has been clamped and stretched, segment windows are cut out. The spacing and position of the windows for a specific cuff is previously determined. The distance between conductive segments varies with the specific application. Alternately, the windows may be cut out before stretching provided due account is made for the different geometrical conditions.

The next step is to place the conducting material, e.g., platinum foil 0.001 inches thick, over the windows. Gold, conductive polymers or other biocompatible conductors may also be used. The length and width of the foil exceed the dimensions of the windows by a small amount, e.g., 0.02 inches each direction. The stimulating portion of the conductive segments 40, 50 is only that region exposed through the windows. The platinum foil segments are connected to the stimulator via electrical conductors, e.g., metals and conducting polymers 42, 52 which are spot-welded or otherwise connected to the platinum. Alternately, the platinum foil which forms the electrodes can extend integrally the entire length of the cuff. The wire or foil extends lengthwise down the cuff to the end and is later connected to lead wires from the stimulator by spot-weldinig or soldering. Epoxy or silicone rubber is used to insulate the exposed metal. Alternately, cuffs and lead wires may be connected and formed in a single step prior to mounting on the cuff.

After the conducting surfaces 40, 50 have been positioned, a thin layer of uncured silicone elastomer or adhesive is spread over the entire surface of the stretched sheet and the metal foil lying on top of it. The second silicone elastomer sheet 32 is then carefully placed on top of this. Another steel plate is then placed over the entire configuration and clamped down to the bottom plate with screws. Shim stock is used to obtain an overall thickness of the cuff of about 0.011 inches. The assembly is placed in an oven and heated for about 30 minutes to allow the silicone elastomer to cure fully. After cooling, the cuff is removed and the edges trimmed to the proper dimensions determined for the specific application. The cuff curls naturally.

The predominant curling characteristic of the cuff is achieved by stretching the first sheet as described above. The stiffness of the metal within the cuff allows some plastic deformation by hand which can be used to increase or decrease the natural diameter of a particular cuff slightly. Hence, exact measurements are not essential. The diameter of the curl of an electrode can typically be altered by about 10%–15%. Once the cuff has been implanted at a specific diameter, small amounts of swelling of the tissue within the cuff will cause a similar expansion by the cuff due to its spiral nature. This reduces the risk of tissue trauma. The cuff thus has the advantage that slight variations of the tissue will be automatically accounted for by the cuff, reducing the risk of damage to the nerve.

An example of the specific dimensions which produce a suitable cuff is as follows: A sheet of cured silicone elastomer, 5.3 inches long, is stretched to a length of 6 inches. The platinum foil and leads are laid down after 0.3 to 0.5 inch windows have been exposed. The uncured adhesive layer is applied and a second cured sheet of silicone rubber, 6 inches long, is placed on top of it. The cured sheets are both 0.005 inches thick. The total thickness of the cuff is 0.011 inches as it is compressed between the two steel plates with appropriate shim stock placed between the plates. After curing, the cuff is removed and trimmed. A typical internal cuff diameter is approximately 0.165 inches and the circumference is approximately 0.518 inches. The diameter of the cuff can be varied by manual manipulation from about 0.150 inches to 0.180 inches to adjust it to a particular nerve. The exact window length is selected to correspond to final cuff internal circumference.

FIG. 5 illustrates an alternate embodiment of the present invention in which like elements with the embodiment of FIGS. 1–4 are denoted with the same reference numerals with a primed (') suffix. In the embodiment of FIG. 5, the self-curling sheet A again has oppositely disposed first and second surfaces 10', 12', first and second longitudinally extending edges 14', 16', and first and second transveresly extending ends 18', 20'. A cut out region 22' is defined in a top layer 30'. A second or lower layer 32' is continuous below the cut out region. The first layer 30' is stretched before the second layer is adhered thereto such that as the first layer attempts to contract back to its relaxed state, the differential contraction of its surfaces cause the sheet to curl.

The conductive portions B include an first conductive segment 40' transversely extending across the cut out region parallel to the first end 18'. A second conductive segment 50' is disposed adjacent the first edge 14' and extends parallel to the cut out region 22'.

In the alternate embodiment of FIG. 6, like elements with the embodiment of FIGS. 1–4 are denoted by the same reference numerals but followed by a double prime ("). The sheet A is provided with no cut out region. A conductive segment 40" has sufficient length to extend peripherally around the interior axial passage of the curled cuff. The conductive segment, such as a non-woven polymeric felt, conducts fluid medications therethrough. At least an exposed upper surface of each segment is porous to enable medicaments to diffuse therefrom into surrounding tissue. A conductive lead 42" defines an axial internal passage for conducting medicinal fluids, such as liquids, gases, suspensions, and the like, to the porous, conductive segment 40". One or more additional conductive segments, such as a second segment 50" shown in phantom, may be disposed along the first end of the sheet. Alternately, the conductive segment may be infused with a full dose of the medication to be time released and the conductive lead eliminated.

The invention has been described with reference to the preferred embodiments. Obviously, modifications and alterations will occur to others upon reading and understanding the preceding detailed description of the preferred embodiments. It is intended that the invention be construed as including all such alterations and modifications insofar as they come within the scope of the appended claims or the equivalents thereof.

Having thus described the preferred embodiments of the invention, the invention is now claimed to be:

1. An implantable cuff for encircling internal body tissues, the cuff comprising:
   a self-curling sheet of non-conductive material which includes a first layer and a second layer, the first layer being resiliently extensible, the second layer being bonded to the first layer such that it tends to hold an interface therebetween extended, such that resilient contractive forces of the first layer bias the sheet to curl into a non-conductive sleeve portion;
   at least one conductive segment disposed adjacent one longitudinally extending edge of the self-curling sheet.

2. The implantable cuff as set forth in claim 1 wherein the conductive segment extends transverse to said one edge.

3. The implantable cuff as set forth in claim 2 wherein the conductive segment has a length which is commensurate with an interiorly defined periphery of the curled sheet.

4. The implantable cuff as set forth in claim 1 wherein the conductive segment is electrically conductive and further including an electrically conductive lead extending therefrom.

5. An implantable cuff for diffusing medications into encircled internal body tissues, the cuff comprising:
   a self-curling sheet of non-conductive material which is self-biased to curl into a tubular spiral, defining a non-conductive sleeve portion encircling internal body tissues;
   at least one porous fluid conductive segment disposed adjacent one longitudinally extending edge of the self-curling sheet for conducting fluid medication therethrough and diffusing the fluid medication into the encircled internal body tissues.

6. An implantable cuff for encircling a nerve trunk or other internal body tissue, the implantable cuff comprising:
   a generally flat self-curling sheet defining:
      (i) a first layer and a second layer, the first layer being resiliently extensible, the second layer being bonded to the first layer such that it tends to hold an interface therebetween extended, whereby resilient contractive forces of the first layer bias the sheet to curl,
      the sheet being self-biased to curl around an axis extending longitudinally generally parallel to the first edge into a spiral with the first layer in part defining an interior periphery of an axial passage therethrough and the second planar surface in part defining an exterior periphery;
   a conductive segment disposed on the first layer surface adjacent the first edge.

7. The cuff as set forth in claim 6 wherein the first layer is elastomeric.

8. The cuff as set forth in claim 7 wherein the first layer is a silicone rubber.

9. An implantable cuff for encircling a nerve trunk or other internal body tissue, the implantable cuff comprising:
   a generally flat sheet of non-conductive material, the sheet defining:

(i) first and second generally planar surfaces on opposite faces thereof,
(ii) first and second oppositely disposed edges,
(iii) first and second oppositely disposed ends,
(iv) a cut out portion adjacent an intersection between the first end and the first edge,
the sheet being self-biased to curl around an axis extending longitudinally generally parallel to the first edge into a spiral with the first edge within the spiral and the first planar surface in part defining an interior periphery of an axial passage therethrough with the second edge outside of the spiral and the second planar surface in part defining an exterior periphery such that as the sheet curls, the cut out region defines an enlarged portion of the axial passage; and,
a conductive segment disposed on the first planar surface adjacent the first edge.

10. The cuff as set forth in claim 9 wherein the self-curling sheet includes at least two layers, at least one of which is eliminated in the cut out region.

11. The cuff as set forth in claim 9 wherein the conductive segment is a first electrode.

12. The cuff as set forth in claim 11 further including a second electrode extending from the cut out region generally parallel to the first end.

13. The cuff as set forth in claim 12 wherein the first and second electrodes are both disposed closer to the first end than to the second end.

14. The cuff as set forth in claim 11 wherein the first electrode is disposed closer to the first end than the second end, such that when the electrode functions as a cathode, more current flows from the first end to the electrode than from the second end to the electrode.

15. The cuff as set forth in claim 11 wherein the first electrode is a layer of conductive polymer.

16. The cuff as set forth in claim 11 wherein the first electrode is a metal layer.

17. An implantable cuff for infusing medication into encircled internal body tissue, the implantable cuff comprising:
a generally flat sheet of material, the sheet defining:
(i) first and second generally planar surfaces on opposite faces thereof,
(ii) first and second oppositely disposed edges,
the sheet being self-biased to curl around an axis extending longitudinally generally parallel to the first edge into a spiral with the first edge within the spiral and the first planar surface in part defining an interior periphery of an axial passage therethrough and with the second edge outside of the spiral and the second planar surface in part defining an exterior periphery; and,
a medication conductive segment disposed on the first planar surface adjacent the first edge for conducting medications therethrough for infusion into the encircled body tissue.

18. The cuff as set forth in claim 17 further including a fluid conducting lead operatively connected with the conductive segment for conducting medication thereto.

19. A method of installing an cuff around internal body tissue, the method comprising:
unrolling a cuff which includes a self-curling sheet of non-conductive material, which sheet is self-biased to curl into a spiral and which cuff includes at least one conductive segment disposed adjacent a first edge of the sheet;
positioning the sheet first edge adjacent the internal body tissue to be encircled;
controlledly permitting the self-curling sheet to curl around the internal body tissue into a tubular spiral.

* * * * *